United States Patent [19]

Spencer

[11] Patent Number: 4,507,119
[45] Date of Patent: Mar. 26, 1985

[54] STERILE DOCKING PROCESS, APPARATUS AND SYSTEM

[75] Inventor: Dudley W. C. Spencer, Wilmington, Del.

[73] Assignee: E. I. Du Pont de Nemours and Company, Wilmington, Del.

[21] Appl. No.: 395,794

[22] Filed: Jul. 6, 1982

[51] Int. Cl.³ .............................................. A61M 25/00
[52] U.S. Cl. ..................................... 604/280; 604/905; 156/152; 156/304.2; 264/248
[58] Field of Search .................... 604/905, 29, 280; 156/158, 159, 296, 502, 503, 304.2, 304.3, 304.5, 152; 264/156, 141, 248

[56] References Cited

U.S. PATENT DOCUMENTS 4,047,691 10/1983 Ishii .................................... 156/304.2
4,256,689 5/1981 Jeffrey ............................... 156/304.2
4,369,779 1/1983 Spencer ......................... 156/304.2 X

OTHER PUBLICATIONS

*Modern Plastic Encyclopedia,* 1979–1980, p. 432.
*Plastics Technology,* Bell Communications, Inc., N.Y., 1980–1981, p. 242.

*Primary Examiner*—Stephen C. Pellegrino

[57] ABSTRACT

A process, apparatus and system for making a sterile connection between two thermoplastic resin tubes is disclosed. A hot stream of fluid is urged either through both said tubes transversely of the axis of each tube or through opposing side sections of the tubes substantially perpendicular to the axes of the tubes to form continuous contact between the hot fluid stream, the interior of the tubes and molten tube portions thereby formed. The tubes are aligned with each other, if necessary, and urged together while the hot fluid stream is removed. As the thermoplastic resin cools a sterile weld is formed.

28 Claims, 19 Drawing Figures

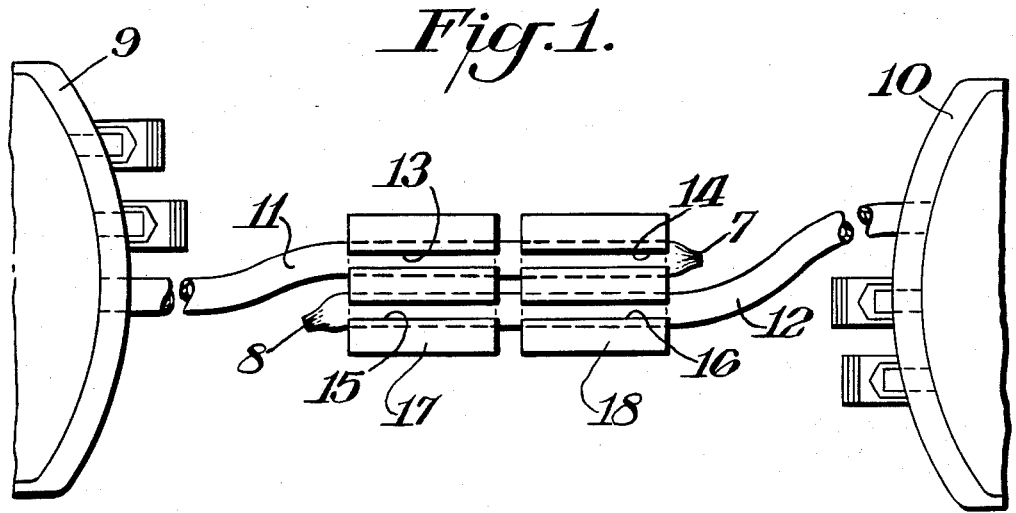
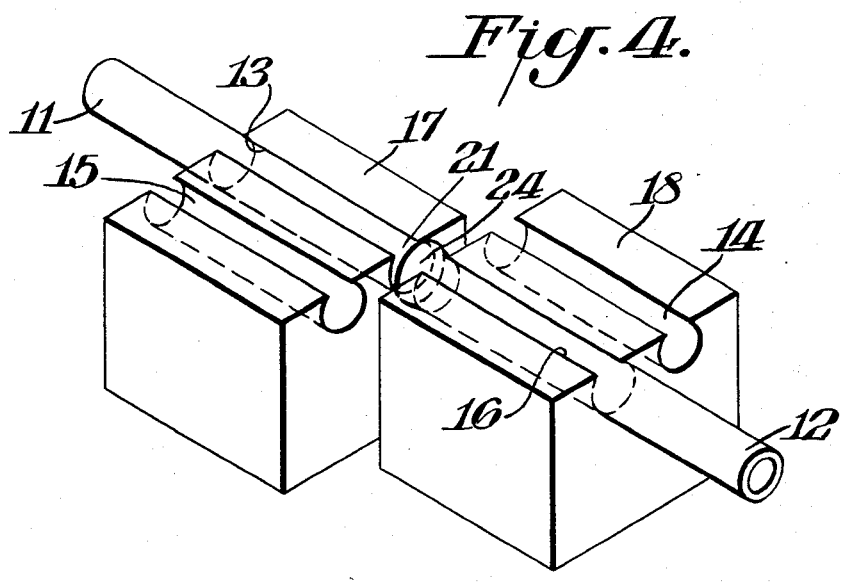
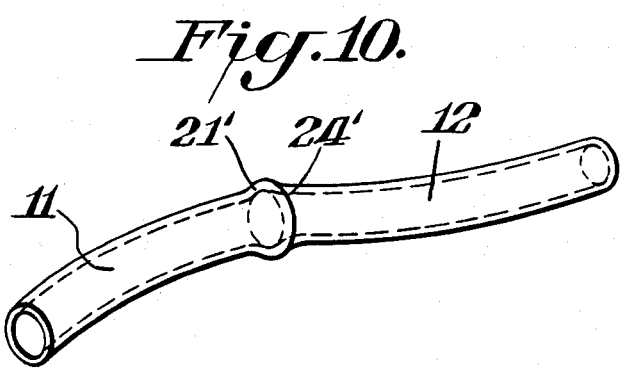

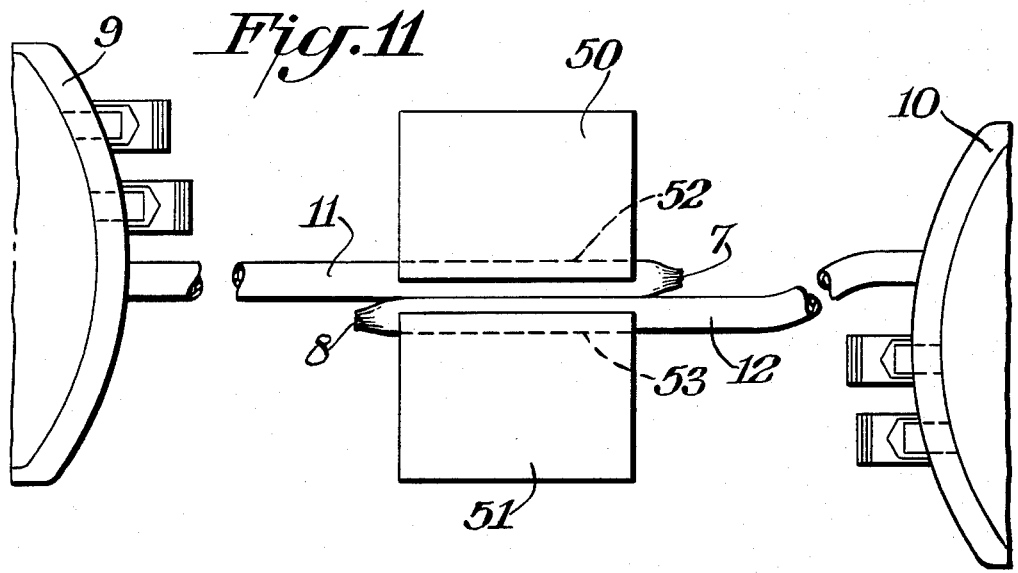
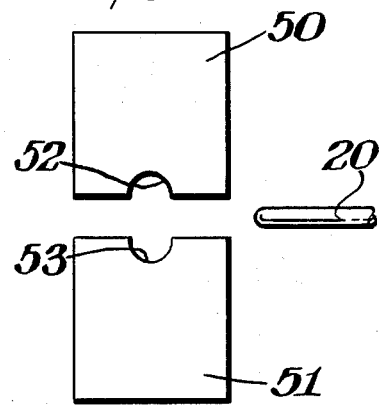
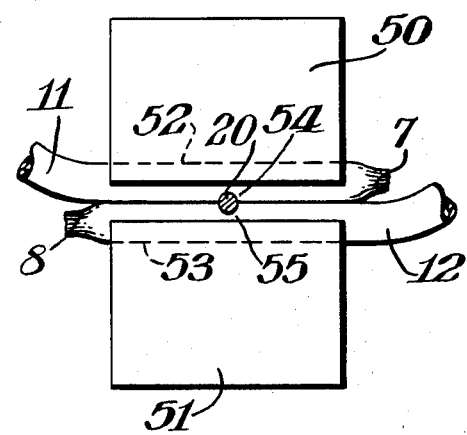
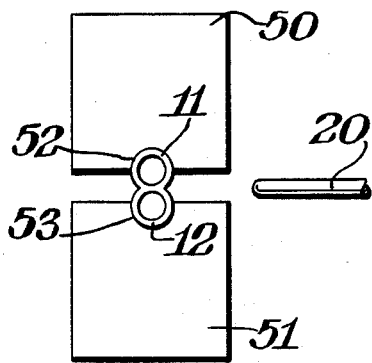
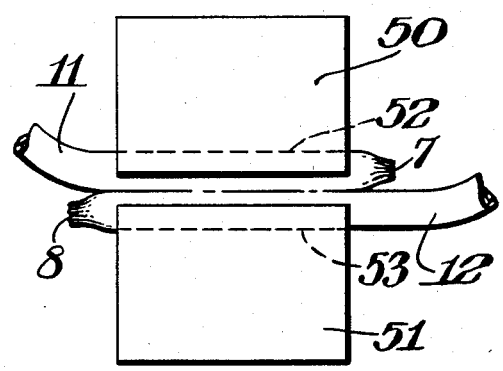

STERILE DOCKING PROCESS, APPARATUS AND SYSTEM

BACKGROUND OF THE INVENTION

Field of the Invention

This invention relates to a process, apparatus and system for forming a sterile connection (sterile docking) between two tubes.

At the present time there are a number of medical and scientific procedures which require the sterile transfer of fluids from one container to another. The only truly sterile transfer system in current use involves prejoining containers with tubes and then sterilizing the entire assembly. This is inflexible and costly since new containers cannot be added and the number of joined containers needed is often not known at the time of initial filling.

An example of the need for sterile docking is in continuous ambulatory peritoneal dialysis (CAPD). This procedure is replacing dialysis of blood outside the body in membrane diffusion cells where waste products normally removed by kidneys are washed from the blood, which is then returned to the patient. Dialysis outside of the body is a time-consuming procedure and sometimes results in damage to the blood by exposure to materials and conditions external to the body. In CAPD, the patient is required to spend time only for draining spent dialysate and replacing it with a fresh solution.

The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposes the tube ends to airborne bacteria or other contamination even though precautions are taken. No satisfactory way heretofore has existed to insure sterility in spite of the elaborate and costly precautions now employed including the use of masks, gloves, gauze strips and disinfectant solutions. Usually contamination does occur to the extent that a case of peritonitis is contracted perhaps on the average once or more a year and scar tissue from it inhibits dialysis.

Truly sterile connections could minimize the occurrence of peritonitis. Also any other treatment bags, such as for an antibiotic, bacteriostat, or other medication, could be connected as desired.

A similar need for sterile docking exists for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers, stabilizers for cell metabolism, other preservatives, or rejuvenants; or washes to remove a treating agent or other contaminant. Actually, it is not feasible to have preconnected bags for all the treatments which may be desired. Supplemental treatments such as fresh preservative cannot now be added sterilely during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood factions. The main reason for the current limited use is that heretofore any entry into a sterile blood unit exposed the blood to bacteria, thereby requiring that the blood be used within 24 hours from entry. Hence, although the viability of stored blood components can be extended by supplemental treatments, such as adding a preservative during storage, such treatments are usually not effected.

Moreover, the primary blood bag contains anticoagulant which can be sterilized only by heat (steam); thus all preconnected bags are also sterilized by wet-sterilization techniques, i.e., steam or hot water in an autoclave apparatus. These bags are made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not now used in preconnected systems.

A sterile docking means would permit one to effect whatever processing is desired without compromising sterility, limiting storage life or requiring the preconnection of a multitude of bags, all wet-sterilizable, without knowing which, if any, will be used.

References

U.S. Pat. No. 3,013,925 discloses a method of welding two joints of thermoplastic pipe wherein the inside of each end of the joints of pipe to be welded is beveled and the ends of the pipes are heated, for example by pressing the ends of the sections of pipe against a heated plate, after which the ends of the sections are forced together so that flow of softened material is to the outside of the pipe and a weld is effected substantially without formation of a bead on the inside of the welded pipe.

U.S. Pat. No. 3,035,631 discloses a tip for welding plastic parts. The tip has a knife edge at each of two opposing ends. One end of the knife is thick whereas the other is thin. The patent states that as the thin end passes through the joint, it will induce molten plastic surfaces to flow together.

U.S. Pat. No. 3,117,903 discloses a method of joining thermoplastic pipe without forming a troublesome inside ridge at the point of weld, said method involving the immersion of the ends of pipe to be welded in inert high boiling organic liquid heated above the softening temperature of the polymer forming the pipe. Thereby, the ends of the pipe are caused to expand and flare outwardly; then the pipe is withdrawn from the bath and the ends butted together.

U.S. Pat. No. 3,897,296 discloses a method of welding two plastic surfaces together by juxtapositioning the surfaces, heating the surfaces to a temperature approaching the flash point of the plastic surfaces to liquefy the surfaces, removing a portion of the liquefied surfaces to expose unoxidized surfaces therebeneath and immediately bringing the unoxidized surfaces into abutment with one another. The patent is silent as to cutting a tube as well as forming a sterile dock.

U.S. Pat. No. 3,968,195 discloses a method for making a sterile connection between two rigid tubes the free ends of which have thermoplastic diaphragms which seal them off. The free ends of each rigid tube are aligned while being spaced slightly apart, and each thermoplastic diaphragm is opened by heating. The free ends of the rigid tubes are then brought into contact and held in position under a slight pressure while the thermoplastic material cools and solidifies, thereby creating a permanent connection. This process requires tubes which have low-melting thermoplastic diaphragms on the ends which can only be used once, i.e., another connection to the same tubing cannot be made.

U.S. Pat. No. 4,209,013 discloses an improvement in a sterile connector system for continuous peritoneal dialysis in which a dialysis solution container having a transfer port is coupled to tubing extending from a patient's peritoneal cavity. The improvement comprises a flexible housing having a first area thereof for attachment to the transfer port and a second spaced area for attachment to the patient's tubing. The attachment areas define openings for enabling the transfer port and patient's tubing to extend within the interior of the flexible housing when they are attached thereto. The flexible housing has means for receiving a sterilizing fluid therein and is operable to enable the transfer port and the patient's tubing to be sterilized within the housing and also connected to each other within the housing.

U.S. Pat. No. 4,223,675 discloses a system for producing sterile, non-autoclavable body fluid containers having autoclaved liquid therein, comprising a dry-sterilized package formed of a material which is unsuitable for being subjected to autoclave conditions, said dry-sterilized package including a sterile communication with the interior of said package; an autoclavable dispenser constructed of an autoclavable substance and containing liquid which was sterilized within the dispenser, said dispenser including a sterile connector having an initially closed sterile aperture in sterile communication with the interior of the dispenser; said package sterile connector and said dispenser sterile connector being in mating engagement with each other.

"An Aseptic Fluid Transfer System for Blood and Blood Components", B. A. Myhre et al, Transfusion, Vol. 18, No. 5, pp. 546-552, Sept.-Oct. 1978, describes a process for heat sealing two aseptic fluid transfer system (AFTS) units together. The AFTS units contain a layer of Kapton ® film (an aromatic polyimide resin which is stable at relatively high temperatures). A pair of dies, one of which is flat and one of which has a raised "H" shaped area, are brought together under a pressure of 100 psi ($6.9 \times 10^6$ dynes per square centimeter) with the AFTS units disposed between the dies. The temperature of the dies is raised to 200° C. (392° F.) over a period of 45 seconds. The dies are withdrawn and upon removal of the AFTS units from the dies, the AFTS units are heat sealed together by a seal surrounding an opening between the AFTS units. Blood bags constructed with an AFTS unit attached can thereby be joined. This system is slow and requires specially constructed units that can only be used once.

Other patents directed to sterile connection apparatuses or methods include U.S. Pat. Nos. 4,157,723, 4,242,310 and 4,253,500.

SUMMARY

The present invention relates to a process, apparatus and system for joining two sterile, closed end tubes or conduits using a hot stream of fluid while maintaining system sterility. The process comprising juxtaposing the tubes, (1) urging a hot stream of fluid either through both said tubes transversely of the axis of each tube or through opposing side sections of said tubes substantially perpendicularly to the axis of said tubes, thereby providing continuous contact between the hot fluid stream, the interior of each tube, and molten tube portions thus formed and (2) urging the molten portions of said tubes together to form a joint between the tubes while removing said hot stream. The hot stream of fluid is at a temperature high enough to kill bacteria with no chance for viable airborne or surface bacteria to find their way inside either of the tubes or the joint. When the joint cools, the sterile connection or docking is complete. This joint is sound and strong and a number of additional joints can be made in subsequent dockings with the same tube. The invention provides a quick, inexpensive system with no special fittings permitting maximum flexibility in processing, storing and using sterile fluids.

BRIEF DESCRIPTION OF THE DRAWINGS

FIG. 1 is a plan view of mounting blocks used to hold two tubes which are to be joined in the starting position.

FIG. 4 is a perspective view of the mounting blocks and welded tubes.

FIG. 10 is a perspective view of the welded tubes.

FIG. 11 is an end view of the mounting blocks used to hold two tubes to be joined in another embodiment of the invention which is further illustrated in FIGS. 12-18.

FIG. 12 is a side view of the mounting blocks and elongated body.

FIG. 13 is a side view of the mounting blocks, elongated body and two tubes to be joined shown in cross section.

FIG. 14 is an end view of the mounting blocks, two tubes to be joined and the hot elongated body.

FIG. 15 is an end view of the mounting blocks and welded tubes.

DETAILED DESCRIPTION OF THE INVENTION

Figure 2:
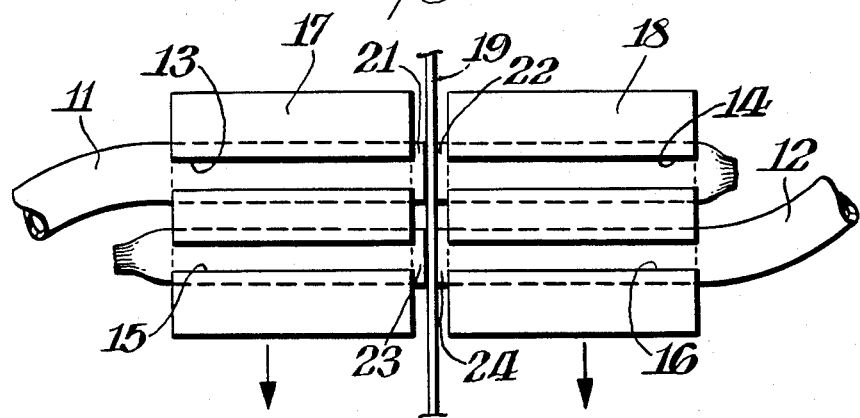
FIG. 2 is a plan view of the two tubes being severed by a hot stream of fluid.

Referring now to FIG. 1 the sealed end 7 of thermoplastic tube 11 is inserted in slots 13 and 14, machined in blocks 17 and 18. The sealed end 8 of tube 12 is inserted in slots 15 and 16, machined in blocks 17 and 18. Slots 13-14 and 15-16 are aligned to receive straight tubing ends. In FIGS. 1-4, tubes 11 and 12 are connected to blood bags 9 and 10. Alternately, one of said tubes may be connected to a dialysis bag and the other to the patient's peritoneal cavity. Also, the tube which is connected to the patient's peritoneal cavity may be connected at the other end to an empty bag in lieu of having a sealed end.

Referring now to FIG. 2, a hot steam of fluid 19, which in this figure is air, has melted through tubes 11 and 12 and there are now four molten tube ends 21, 22, 23 and 24. The hot stream of fluid in contact with these molten ends prevents any disruption of the sterility in the interior of tubes 11 and 12.

Figure 3:
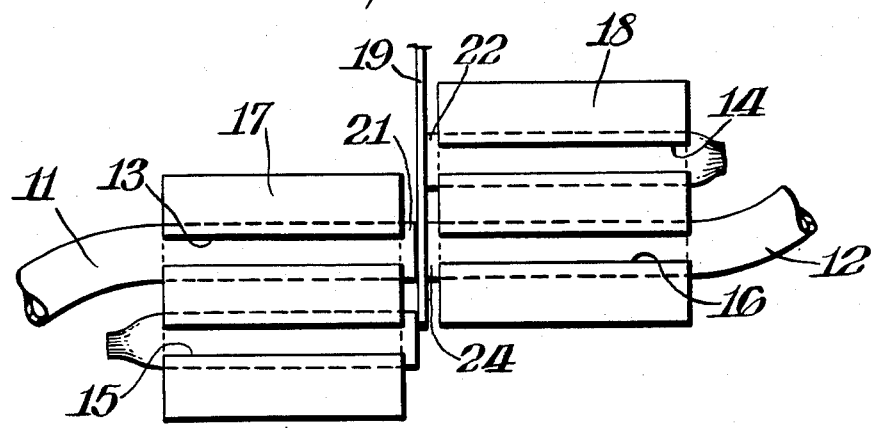
FIG. 3 is a plan view of the two tubes being repositioned and aligned opposite each other.

Referring now to FIG. 3, block 17 has been moved relative to block 18 so that slots 13 and 16 along with tubes 11 and 12 are aligned on opposite sides of the hot stream of fluid 19.

Referring now to FIG. 4, the hot stream of fluid has been shut off and molten tube ends 21 and 24 have fused, thereby joining tubes 11 and 12 together. The blocks 17 and 18 holding tubes 11 and 12 were urged together and just as tubes 11 and 12 met the hot stream of fluid was shut off. The tubes were urged together by a spring (not shown) resulting in a slight compression of the joint.

Figure 5:
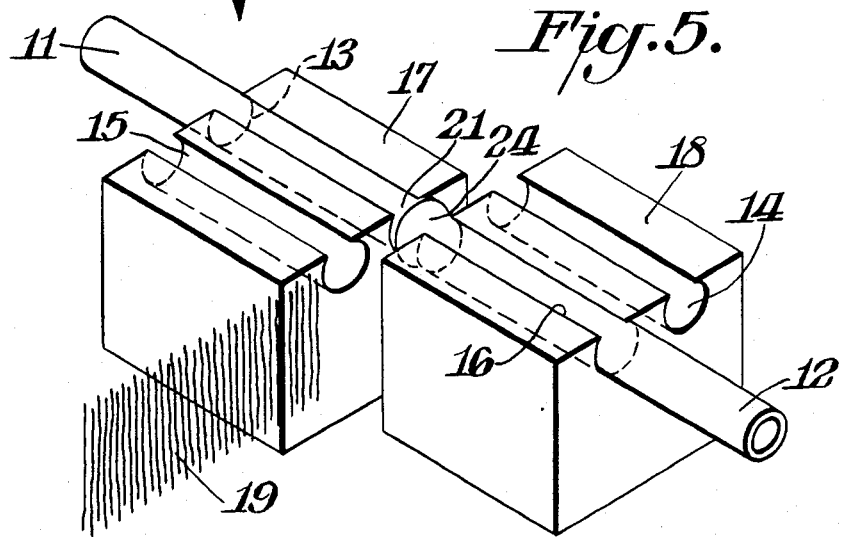
FIG. 5 is a perspective view of the mounting blocks, hot fluid stream, and welded tubes.

FIG. 5 illustrates another embodiment of the invention. In this embodiment, blocks 17 and 18, with slots 13 and 16 and tubes 11 and 12 still aligned, and hot stream of fluid 19 have been moved relative to each other and the molten tube ends 21 and 24 have fused and thereby joined tubes 11 and 12 together. The blocks 17 and 18 holding tubes 11 and 12 were urged together by a spring (shown in FIG. 6) during the time when they and cutting means 19 were being moved relative to each other, resulting in a slight compression of the joint.

Figure 6:
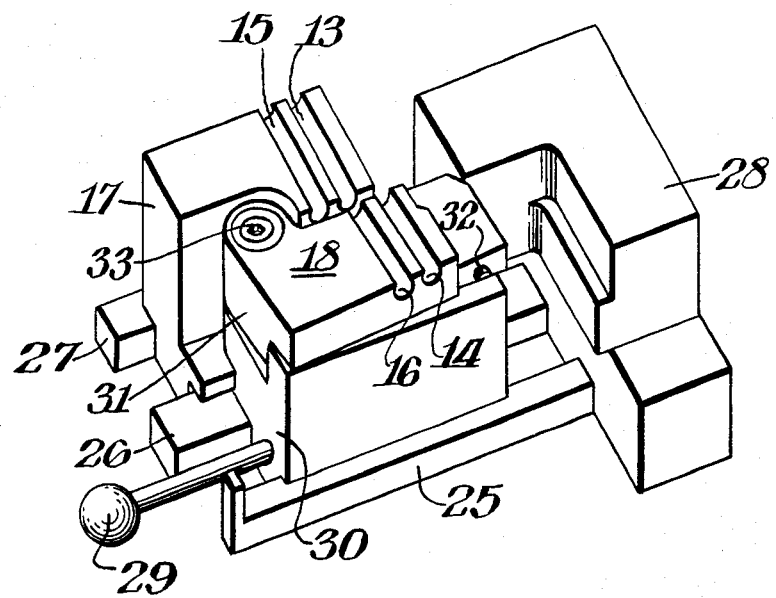
FIG. 6 is a perspective view of the mounting blocks slidably mounted on their guides.

Referring now to FIG. 6, blocks 17 and 18 are shown with slots 13 and 16 aligned and the block in the position after the weld has been made and the welded tubes removed. The blocks are shown slidably mounted in guides 25, 26 and 27. Block 18 is shown as two parts 30, 31 which are connected together by bolt 33 so as to allow rotational motion of part 31. Thereby, part 31 can be individually urged by spring 32 toward block 17 as the blocks and tubes (not shown) held thereby are withdrawn from the stream of fluid (not shown for clarity).

Figure 8:
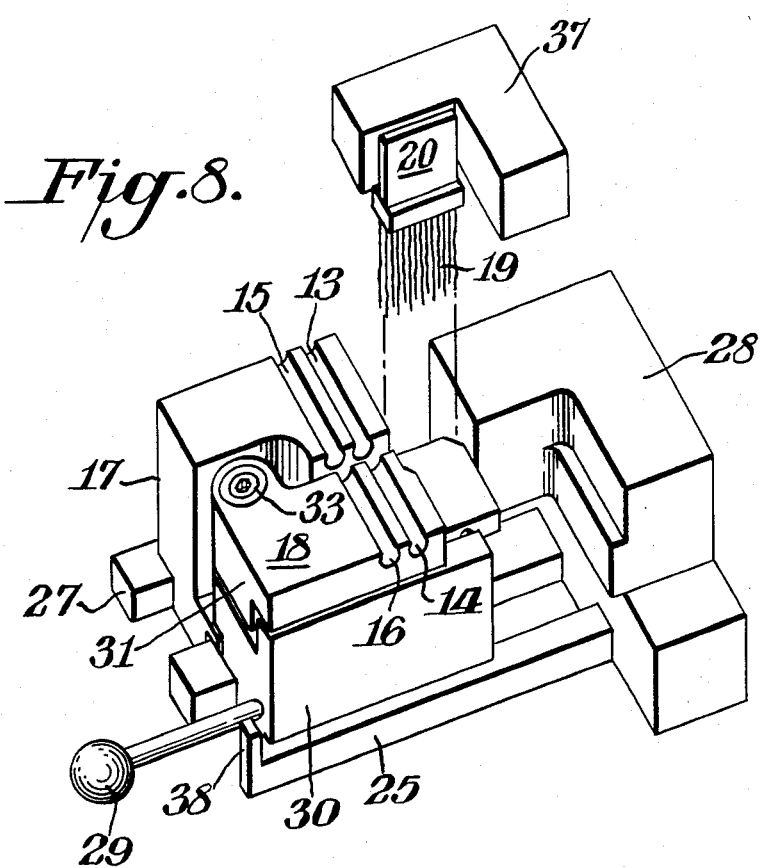
FIG. 8 is a perspective view of the mounting blocks, slidably mounted on their guides and fluid jet.
Figure 9:
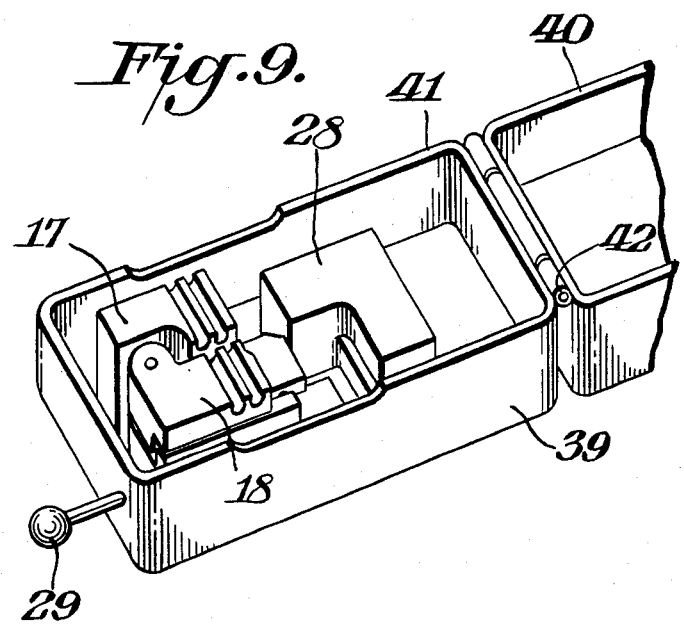
FIG. 9 is a perspective view of the mounting blocks fixedly arranged in a housing.

FIG. 6 also shows operating handle 29 and stop-block 28 against which mounting blocks 17 and 18 are pushed. Operation of this embodiment is best described by using FIGS. 6-9 along with reference to FIGS. 1-3 already described. The operator inserts tube ends in slots 13-14 and 15-16 as shown in FIG. 1. Fluid jet 20 shown in FIG. 8 is activated thereby causing hot fluid stream 19 to pass between stop-block 28 and mounting blocks 17 and 18 in alignment with the space between said mounting blocks. Positioning of fluid jet 20 is effected by having the jet mounted on block 37 which is fixedly arranged in the upper portion 40 of housing 39 shown in FIG. 9 and the mounting blocks, stop-block 28 and the accompanying slides fixedly arranged in a base portion 41 of housing 39 so that when the housing is closed the fluid jet is properly situated. The two sections of the housing are attached by hinge 42.

Figure 7A:
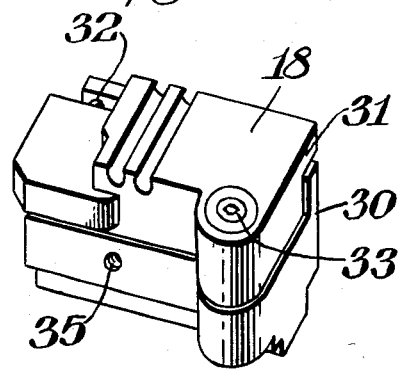
FIGS. 7A and B are perspective views of the mounting blocks.
Figure 7B:
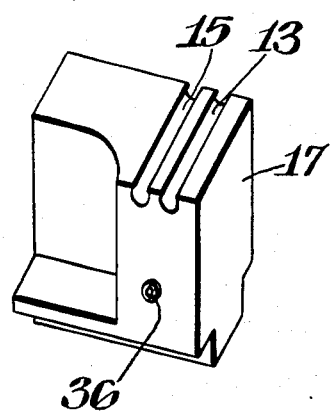

Blocks 17 and 18 shown in FIGS. 7A and B fit together so that the foremost horizontal faces are adjacent. When in the starting position, the nounting blocks are kept in a cooperative relationship by pressure fit of threaded pin 36 on block 17 into cavity 35 in block 18 (FIGS. 7A and B). The operator pushes handle 29 which moves blocks 17 and 18 together on slides 25, 26 and 27, thereby moving the tubes across hot fluid stream 19 as shown in FIG. 2. Block 17 strikes stop-block 28 first thereby causing the two blocks to become sufficiently disengaged so that block 18 moves on to stop against stop-block 28. This further movement by block 18 aligns slots 13 and 16 as shown in FIG. 3. The operator immediately withdraws handle 29 to move block 18 which is connected to the handle 29 and, by friction between the blocks through the pressure exerted by pin 36 on block 18, block 17 also. The blocks and the tube ends to be joined move back away from hot fluid stream 19. As the corner of block 18 leaves the edge of block 28, spring 32 urges part 31 of block 18 to rotate slightly about bolt 33 toward block 17 so that slight compression is urged on the tube ends being joined as they move away from the edge of the hot fluid stream (see FIG. 6). Stop 38 (FIG. 8) on slide 25 completes the motion of blocks and handle. The operator removes the joined tube after about 5 seconds delay for the joint to cool.

Referring now to FIG. 10, tubes 11 and 12 are shown joined at now fused molten ends 21' and 24' to form a joint which is slightly enlarged due to the pressure exerted by spring 32. The mode of operation just described is herein called the "transverse severing mode".

Another embodiment of the invention is illustrated in FIGS. 11-18, the herein called "lateral piercing mode". In this embodiment the two tubes to be joined are positioned in a contiguous substantially parallel position and a hot stream of fluid is urged through opposing side sections of said tubes substantially perpendicularly to the axes of the tubes. Referring now to FIG. 11, sealed end 7 of thermoplastic tube 11 is inserted in slot 52, machined in block 50. Sealed end 8 of tube 12 is inserted in slot 53, machined in block 51. The other ends of the tubes are connected to blood bags 9 and 10 or are otherwise connected as described for FIG. 1.

Referring now to FIG. 12, blocks 50 and 51 are shown with slots 52 and 53, respectively, which are each slightly deeper than the radius of the tube to be held so that the tubes are held in the blocks before the blocks are urged together. Referring now to FIG. 13, tubes 11 and 12 are slightly compressed together by blocks 50 and 51 by means of force applied to the blocks. Suitable force can be provided by hand operation or by appropriate mechanical means such as a cam and spring.

Referring now to FIG. 14, fluid jet 20 (see FIG. 18) has been activated to give hot fluid steam 19 which has melted through adjacent side portions of tubes 11 and 12 creating molten tube portions 54 and 55. These molten tube portions provide continuous fluid contact with the interior of tubes 11 and 12. The interior of each tube is maintained sterile by the hot fluid stream passing over the respective molten tube portions.

Figure 16:
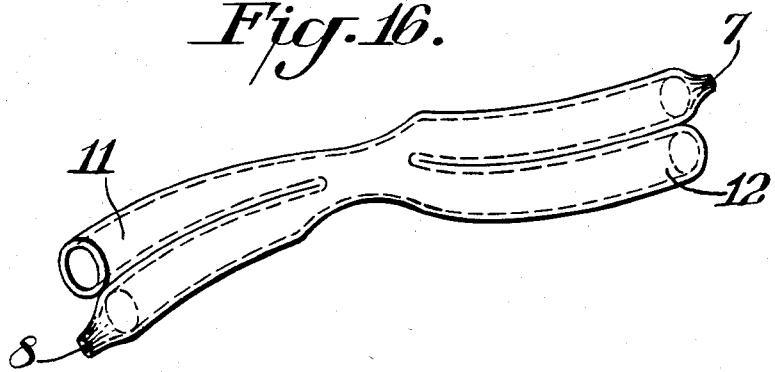
FIG. 16 is a perspective view of the welded tubes.

Referring now to FIG. 15, blocks 50 and 51 have been moved closer together, while the hot fluid stream was removed, to cause molten tube portions 54 and 55 to fuse and thereby join tubes 11 and 12. Referring to FIG. 16, joined tubes 11 and 12 which have been removed from mounting blocks 50 and 51 show a depression opposite the place where the joint was made.

Figure 17:
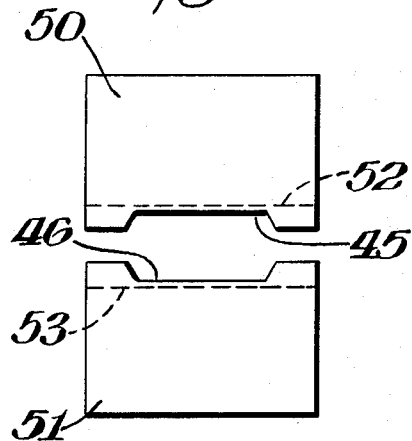
FIG. 17 is an end view of another embodiment of the mounting blocks.

Referring to FIG. 17, a preferred embodiment of blocks 50 and 51 is shown wherein slots 52 and 53 extend deeper than the tube radius only at the extremities of the blocks, thereby providing spaces 45 and 46 which give clearance for the hot fluid stream when additional room is necessary.

Figure 18:
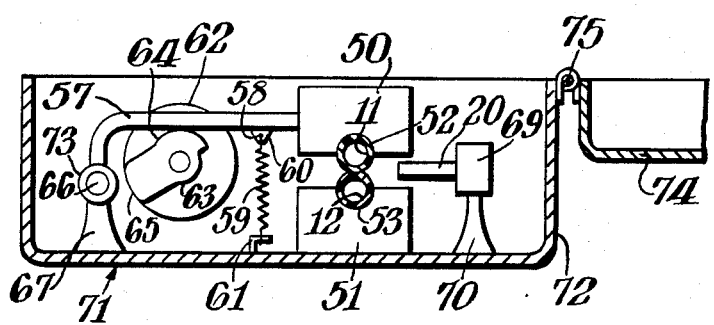
FIG. 18 is a side view of the mounting blocks, hot elongated body, and associated elements of the apparatus arranged in a housing shown in cross section.

FIG. 18 illustrates further this embodiment for carrying out the present invention. In this embodiment tubes 11 and 12 are placed in slots 52 and 53, machined in blocks 50 and 51, respectively. Block 51 is attached to arm 57 which pivots about bolt 66 via collar 42. Bolt 66 is fixedly attached to pedestal 67 which in turn is mounted to base 71 of housing 72. The tubes 11 and 12 are slightly pressed together by means of spring 59 pulling on arm 57. Spring 59 is attached to arm 57 by being hooked thereto at hole 58 in flange 60 and is attached to base 71 by hook 61. Cam 62 imparts three positions to block 50. In the first position, determined by step 65, the blocks are wide open. In the second position, determined by step 64, block 50 is lowered by spring 59 to press tubes 11 and 12 slightly together. In the third position, determined by step 63, block 50 is lowered further to seal the two tubes together. The cam can be manually operated or driven by a DC motor.

Jet 20 is mounted on block 69 which is fixedly attached to pedestal 70 mounted on base 71. Block 51 is also fixedly attached to base portion 71 of housing 72. The upper portion of housing 72 is optional and serves to close the operation from the outside environment. The two portions of housing 72 are attached by hinge 75.

In operation of this embodiment, after tubes 11 and 12 are inserted in slots 52 and 53, cam 62 originally positioned at step 65 is advanced to step 64 causing the two tubes to be urged slightly together and fluid jet 20 is activated to provide a hot fluid stream. The hot stream melts through the adjacent walls of tubes 11 and 12. As the hot stream is separated from the tubes by deactivating jet 20, cam 62 is moved to step 63 whereby spring 50 is caused to urge molten tube portions 54 and 55 (FIG. 14) together. The joined tubes can be removed after about 5 seconds delay for the joint to cool.

Fluid jets suitable for use in the present invention are well known. Suitable jets are described in *Modern Plastic Encyclopedia,* 1979–80, p. 432 and *Plastics Technology,* Bell Communications, Inc. N.Y., 1980–81, p. 242. For the transverse severing mode, the fluid jet can have a circular or rectangular orifice. Preferably the orifice is rectangular and has a width of from about 0.12 mm to about 0.89 mm (5–35 mils), preferably about 0.25 mm (10 mils). The length of the orifice is preferably about 5.1 mm (0.2 inch). For the lateral severing mode, the cross section of the fluid stream, hence the jet orifice, can have an axis, positioned transverse to the tubes, about at least 50% greater than the sum of the wall thickness of each tube to about 100% of the outer diameter of the tubes or 100% of the outer diameter of the smaller of the two tubes to be joined if the tubes are of different diameters. The axes or diameter of the orifice should be dimensioned so as to provide an opening between the tubes which would not unduly restrict flow of fluid. If the fluid used is gaseous, it should be at a pressure of from about 10 kPa to about 40 kPa, more preferably from about 20 kPa to about 30 kPa, and most preferably about 24 kPa (3.5 psi).

The fluid can be a gas, such as air or an inert gas, a vapor including a vaporized sterilant such as Betadine ® solution, or a flame. Preferably, the fluid is air.

Currently-used blood and dialysis bags and tubes are made of plasticized polyvinyl chloride for flexibility, strength and steam sterilizing. Generally, for these plasticized polyvinyl chloride tubes, the fluid stream will be heated to a temperature of from about 600° F. (310° C.) to 800° F. (427° C.) which is also suitable for most other thermoplastic tubing. The hot fluid stream preferably is at a temperature high enough (1) to kill rapidly (less than one second) any bacteria or bacterial spores on the outside surface of the tubes and (2) to melt rapidly the thermoplastic resin from which the tubes are formed. The tubes are heat-sealed closed at their ends or connected to a bag. The tubes and whatever bag or bags they are connected to will have been sterilized. Below about 500° F. (260° C.) bacteria and bacterial spores are not rapidly killed by the heat from the hot fluid stream. Above about 750° F. (399° C.) most polymers such as plasticized polyvinyl chloride or polyolefins such as polypropylene or polyethylene begin to become too liquid to maintain their form in presence of the hot fluid stream. About 600° F. (316° C.) is the preferred temperature for use with conventional plasticized polyvinyl chloride blood bag tubing. Another upper limit is the temperature where the resin from which the tube is made begins to degrade in the time it is exposed to the hot fluid stream (about 2 seconds). For plasticized polyvinyl chloride and polyolefins the upper limit is about 300° F. (149° C.) above the melting point of the thermoplastic resin from which the tube is made.

For conventional 165 mil (4.2 mm) outside diameter, 10 mils (0.25 mm) thick wall plasticized polyvinyl chloride blood bag tubing, a time of 0.5 to 1.5 seconds for severing or piercing the two tubes has been found to be most satisfactory. For the transverse severing mode, the time for repositioning the tubes to align them is not particularly critical but should not be so slow as to cause degraded polymer to be in the welded joint. The speed of removal of the hot fluid stream is important to minimize degradation and excess melting and 0.1 to 1 second has been found to be satisfactory. After removal of the hot fluid stream, cooling of the tubes takes about 5 seconds and the tubes are then removed from the blocks.

The mounting blocks are made of heat conductive metal and serve as heat sinks to assist rapid cooling of the joint. It is necessary that the tubes be urged toward each other as or before the hot fluid stream is removed. For the transverse severing mode, the space between the blocks and the hot fluid stream is relatively important. For tubes of about 165 mils (4.2 mm) outside diameter, the spacing between each of the blocks and the adjacent periphery of the hot fluid stream should be from about 5 mils (0.13 mm) to 50 mils (1.3 mm), and the preferred spacing between the blocks and the adjacent periphery of the hot fluid stream being from about 10 mils (0.25 mm) to 20 mils (0.51 mm). Above about 20 mils (0.51 mm) and especially above about 50 mils (1.3 mm) the exposed tube ends have too much flexibility and the joint may not be sterile. For tubes very much larger than 165 mils (4.2 mm) appropriately larger spacings can be used.

For the lateral piercing mode, the space between the blocks and the slots in them should be such that the two tubes at least nearly touch each other; preferably, the space is such that the two tubes just touch each other. The space between the blocks adjacent the tubes should be about ⅛ greater than the vertical dimension (with regard to FIG. 18) of the jet orifice. Otherwise, for this mode the space between the blocks is not important.

The tubing used should be formed of a thermoplastic resin which melts at least 50° F. below the temperature at which it begins to degrade in the time exposed to heat in the process of the present invention. The tubes to be connected are preferably of the same diameter but can have different diameters so long as a complete seal having about 50% of the original tube strength can be made. The tubes to be joined can be made of the same material or can be made of compatible resins. "Compatible resins" as used herein means that the melting points of the two materials are close enough so that at the operating temperature both form thick, viscous melts which will flow together to form a single melt phase without polymer degradation or formation of thermal or other chemical reaction products which would weaken or otherwise interfere with formation of the single melt phase and its subsequent cooling and solidification to a strong joint. For example, polyethylene is compatible with polyethylene copolymers and polypropylene.

In order to obtain a secure dock, tubes to be joined must not contain more liquid than a thin film on the walls at or near the locations where they are to be cut and joined. Generally, the length of tubing which is empty of liquid need not be more than about 0.5 to 1 inch (13–25 mm).

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment of the invention the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected and the patient's tube can be joined to a sterile sealed-end tube. It also eliminates the need for the present laborious procedure used to achieve sterility.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port, e.g., having a protective covering and a septum inside the port. The bags can also be connected by joining the blood collection tube of the donor bag to the connection tube of the transfer bag. In another embodiment, the blood collection tube and the connection tube of the transfer bag both have a sealed distal end.

In the preferred embodiment for both the blood bag system and the CAPD system, the donor bag and dialysis bag have, specifically for sterile connection, an additional tube (pigtail) which is connector-free and has a sealed distal end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like. This modified bag is further described in copending U.S. application Ser. No. 267,291, now U.S. Pat. No. 4,369,779 the relevant disclosure of which is incorporated herein by reference. The tube is equipped with means, such as a clamp, to prevent undesired flow of liquid into said tube.

In the present system for the sterile connection of blood bags, the need to pre-assemble bags into a system is eliminated. It is to be understood that the expression "blood bag" as used herein refers collectively to either the donor (primary) bag or the satellite bag. With the present invention satellite bags can be sterilely connected to a donor bag as the need arises. The donor bag can be made from a wet-sterilizable material, such as polyvinyl chloride whereas the satellite bags do not have to be wet-sterilizable but can be made of material which can be sterilized only by dry-sterilization means, such as irradiation or ethylene oxide treatment. For example, the satellite bag can be constructed from $O_2$ permeable polyethylene which would increase platelet viability. Alternatively, the satellite bag can be made from a polyethylene copolymer, a polyethylene laminate, polypropylene, or any other material which is compatible with the material from which the donor bag is constructed. The satellite bag can be made from material which is incompatible with the material from which the donor bag is constructed so long as the tubes to be connected are made of compatible materials. For instance, the donor bag and its tubing can be made from polyvinyl chloride whereas the satellite bag can be made from polyethylene but its tubing made from polyvinyl chloride and solvent welded to the satellite bag. Techniques for solvent welding are well known in the art. Supplemental treatments can be sterilely added and washing to remove treating agents can be sterilely effected. Some practitioners believe hepatitis risks can be reduced by washing red cells without previous freezing.

The sterile docking apparatus of the invention can also be used to provide a system for producing sterile, non-autoclavable body fluid containers having wet-sterilized (autoclaved) liquid therein. The system is similar to that described in U.S. Pat. No. 4,223,675; however, the present apparatus eliminates the need to have special connectors attached to the tubing.

With the present invention a dry-sterilized package can be formed from a synthetic resin material which is unsuitable for being subjected to wet-sterilization conditions but is particularly suitable for prolonged storage of body fluids. The autoclavable liquid is placed in an autoclavable dispenser equipped with an access tube which can then be heat-sealed closed. The dispenser package and liquid are then wet-sterilized in an autoclave. The dispenser package is next sterilely connected to a dry-sterilized container by using the apparatus and process of the invention. The dry-sterilized container can be equipped with a connector-free tube having a sealed distal end, said tube being specifically for sterile connection. After the sterile connection is made the autoclaved liquid is transferred to the dry-sterilized container which is non-autoclavable. If desired, the two containers can be separated by heat sealing the connecting tube while moving the containers apart so that each container is left with a connector-free tube having a sealed distal end. The autoclavable liquid can be an anticoagulant and the autoclavable dispenser package can be constructed from polyvinyl chloride. The non-autoclavable container can be a blood bag constructed from materials such as those previously described herein.

The process of the invention for joining two thermoplastic tubes together comprises (1) urging a hot stream of fluid either through both said tubes transversely of the axis of each tube or through opposing side sections of said tubes substantially perpendicular to the axes of said tubes to form continuous contact between the hot fluid stream, the interior of said tubes and molten tube portions thereby formed; and (2) urging the molten portions of said tubes together to form a joint between said tubes while removing said hot fluid stream. The process of the invention can be carried out using the herein-described specific embodiments of the apparatus of the invention but is not limited thereto. The conditions of operation are those previously set forth herein. Subsequent docks to the same tube can be easily made using the transverse severing mode. For the lateral piercing mode subsequent docks to the same tube can be effected by heat sealing the tube with a Hemitron® device immediately below the joint on the bag side of the tube; cutting off, at the seal just made, the unwanted joint and the bag connected thereby to provide a sealed end on the desired tube; and then connecting the new tube using the lateral piercing mode.

I claim:

1. A process for joining first and second thermoplastic tubes together comprising (1) urging a hot stream of fluid to sever either through both said tubes transversely of the axis of each tube or through opposing side sections of said tubes substantially perpendicular to the axis of said tubes to form continuous contact between the hot fluid stream, the interior of each tube and molten tube portions thereby formed; and (2) urging the molten portions of the first tube and the second tube together to form a joint between said first and second tubes while removing said hot stream.

2. A process for forming a sterile connection between a first tube and a second tube, both formed of a thermoplastic resin, comprising mounting said tubes in a pair of mounting means which hold said tubes in a closely adjacent substantially parallel position; urging a hot stream of fluid to sever through both said tubes, transversely of the axis of each tube, at a rate such that the thermoplastic resin from which said tubes are formed and which is in contact with said hot stream of fluid becomes molten, thereby forming molten ends, said hot stream of fluid being at a temperature sufficient to maintain the molten tube ends and ambient air within their vicinity sterile; aligning molten tube ends of the first tube and the second tube with each other; urging the first tube and the second tube together while removing said hot stream; and cooling the thusly joined tube ends whereby a sterile connection is formed between the first tube and the second tube.

3. A process according to claim 2 wherein the hot stream of fluid is at a temperature above about 260° C.

4. A process according to claim 3 wherein the hot stream of fluid is at a temperature below the temperature where the thermoplastic resin from which the tubes are made begins to degrade in the time used.

5. A process according to claim 4 wherein the hot stream of fluid is air.

6. A process for forming a sterile connection between a first tube and a second tube, both formed of thermoplastic resin, comprising mounting said tubes in a pair of spaced-apart mounting means which hold said tubes in a contiguous, substantially parallel position; urging a hot stream of fluid to sever through opposing side sections of said tubes substantially perpendicularly to the axes of said tubes at a rate that the thermoplastic resin from which said tubes are formed and which is in contact with said stream becomes molten, thereby providing continuous contact between the hot fluid stream, the interior of each tube and molten tube portions thus formed; said hot stream of fluid being at a temperature sufficient to maintain the molten tube portions and ambient air within their vicinity sterile; urging the molten portions of said tubes together while removing said hot stream; and cooling the thusly joined molten tube portions whereby a sterile connection is formed between said tubes.

7. A process according to claim 6 wherein the hot stream of fluid is at a temperature above about 260° C.

8. A process according to claim 7 wherein the hot stream of fluid is at a temperature below the temperature where the thermoplastic resin from which the tubes are made begins to degrade in the time used.

9. A process according to claim 8 wherein the hot stream of fluid is air.

10. An apparatus for forming a sterile connection comprising a fluid jet;

means adapted to heat fluid in said fluid jet;

a pair of mounting blocks spaced apart horizontally and adapted to receive and hold two tubes to be joined;

means to provide movement between said mounting blocks and said fluid jet such that said fluid jet is positioned immediately above where said blocks are spaced apart so that when the jet is operated a fluid stream passes therebetween traversing where the mounting blocks are adapted to receive tubes;

means adapted to separate said fluid stream and said blocks;

means for aligning said blocks to a position where two different tube ends to be joined are aligned with and facing each other; and means for urging said blocks together while separating said blocks and said fluid stream.

11. An apparatus according to claim 10 wherein the fluid jet is an air jet.

12. An apparatus according to claim 11 wherein the blocks are spaced from about 3.8 to 5.1 mm from said fluid stream when said fluid stream is passing between said blocks.

13. An apparatus according to claim 12 wherein the blocks are spaced from about 0.13 to about 1.3 mm from said fluid stream when said fluid stream is passing between said blocks.

14. An apparatus for forming a sterile connection comprising a fluid jet;

means adapted to heat fluid in said fluid jet;

a pair of spaced-apart mounting blocks positioned in facing relationship and adapted to receive and hold two tubes to be joined;

means for positioning said fluid jet immediately above where said blocks are spaced apart so that when the jet is operated a fluid stream passes substantially orthogonally between said mounting blocks and intersects partially transversely where the blocks are adapted to receive said tubes;

means to separate said mounting blocks and said fluid stream; and means for urging said mounting blocks partially together as said mounting blocks and said fluid stream are being separated.

15. An apparatus according to claim 14 wherein the fluid jet is an air jet.

16. A sterile connection system for continuous ambulatory peritoneal dialysis in which a dialysis solution container with a transfer port that includes a segment of tubing is coupled to a tube extending from a patient's peritoneal cavity, wherein the improvement comprises a pair of mounting blocks, spaced apart horizontally and adapted to receive and hold the transfer port tube and the patient's tube; a fluid jet; means to provide movement between said mounting blocks and said fluid jet such that said fluid jet is positioned immediately above where said blocks are spaced apart so that when the jet is operated a fluid stream passes therebetween traversing where the mounting blocks are adapted to receive said tubes; means adapted to heat fluid in said fluid jet; means adapted to separate said fluid stream and said blocks; means for aligning said blocks to a position where two different tube ends to be joined are aligned with and facing each other; and means for urging said blocks together while separating said blocks and fluid stream.

17. A sterile connection system according to claim 16 wherein the patient's tube is connector-free and has a sealed distal end.

18. A sterile connection system according to claim 17 wherein the transfer port tube is connector-free, has a sealed distal end, and is the same diameter as that of the patient's tube.

19. A sterile connection system for joining two blood bags, each bag having a tube which can be used for connection and sterile connection being made by joining said tubes, wherein the improvement comprises a pair of mounting blocks, spaced apart horizontally and adapted to receive and hold the tubes to be joined; a fluid jet; means for providing movement between said mounting blocks and said fluid jet such that said fluid jet is positioned immediately above where said blocks are spaced apart so that when the jet is operated a fluid stream passes therebetween traversing where the mounting blocks are adapted to receive said tubes; means adapted to heat fluid in said fluid jet; means to separate said fluid stream and said blocks; means for aligning said blocks to a position where two different tube ends to be joined are aligned with and facing each other; and means for urging said blocks together while separating said blocks and said fluid stream.

20. A sterile connection system according to claim 19 wherein one of the bags is a donor bag and its blood collection tube is one of the tubes to be joined.

21. A sterile connection system according to claim 20 wherein the two tubes to be joined are of the same diameter.

22. A sterile connection system according to claim 21 wherein the blood collection tube has a sealed distal end.

23. A sterile connection system according to claim 22 wherein the second bag is a transfer bag having a transfer port with a transfer tube and the transfer tube is the other tube to be joined.

24. A sterile connection system according to claim 23 wherein the transfer tube has a sealed distal end.

25. A sterile connection system according to claim 19 wherein one of the bags is a donor bag having, in addition to its blood collection tube, a connector-free tube to be used specifically for sterile connection, said tube having a sealed distal end.

26. A sterile connection system according to claim 25 wherein the donor bag is steam sterilizable and the other bag is a transfer bag made from material which is dry sterilizable only.

27. A sterile connection system according to claim 26 wherein the transfer bag has a connector-free tube having a sealed distal end.

28. A sterile connection system according to claim 27 wherein the two tubes to be connected are of the same diameter.

* * * * *